United States Patent [19]
Sorensen et al.

[11] Patent Number: 5,320,627
[45] Date of Patent: Jun. 14, 1994

[54] METHOD AND DEVICE FOR INTRACORPOREAL DEVICE FOR INTRACORPOREAL MORSELLING OF TISSUE AND/OR CALCULI DURING ENDOSCOPIC SURGICAL PROCEDURES

[75] Inventors: John T. Sorensen, Costa Mesa; John Crease, Huntington Beach; Edmund E. Spaeth, Orange; Joseph F. Rondinone, Mission Viejo, all of Calif.

[73] Assignee: EndoMedix Corporation, Irvine, Calif.

[21] Appl. No.: 32,756

[22] Filed: Mar. 17, 1993

Related U.S. Application Data

[63] Continuation of Ser. No. 639,494, Jan. 9, 1991, abandoned.

[51] Int. Cl.⁵ ............................................ A61B 17/32
[52] U.S. Cl. ..................................... 606/128; 606/127; 606/170; 606/167; 606/180; 604/22; 128/751
[58] Field of Search .............. 606/128, 159, 170, 171, 606/180, 127, 167; 604/22; 128/751, 752

[56] References Cited

U.S. PATENT DOCUMENTS

| | | | |
|---|---|---|---|
| 4,679,558 | 7/1987 | Kensey et al. | 606/128 |
| 4,811,735 | 3/1989 | Nash et al. | 606/128 |
| 4,923,462 | 5/1990 | Stevens | 606/159 |

*Primary Examiner*—Lee S. Cohen
*Assistant Examiner*—Brian L. Casler
*Attorney, Agent, or Firm*—Robert D. Buyan

[57] ABSTRACT

A method and device for reducing the size of tissues and/or other materials contained within an intracorporeally positioned organ or artificial containment sac. In one embodiment, the device comprises an elongate cutting tool having a rotatable cutting head or impactor positioned on the distal end of the tool and, optionally, having one or more aspiration/infusion lumens extending longitudinally through the elongate shaft of the tool. In a second embodiment, the device may comprise (a) a separate guide/aspiration/infusion cannula initially insertable into the organ or sac and (b) a separate elongate cutting device which is insertable through and extractable from the prepositioned guide/aspiration/infusion cannula. An automatically deployable protective assembly may be positioned at the distal tip of either embodiment of the device so as to form a protective cage around the rotatable cutting head or impactor. Such protective cage is configured to prevent the cutting head or impactor from causing damage to the surrounding organ or sac. This invention also includes an artificial containment sac which may be inserted into a body cavity through a natural opening or small incision and which may subsequently be utilized as a bag-like container for tissues, organs, tumors, calculi or other materials which are to be treated by the device of the invention and removed from the body.

36 Claims, 8 Drawing Sheets

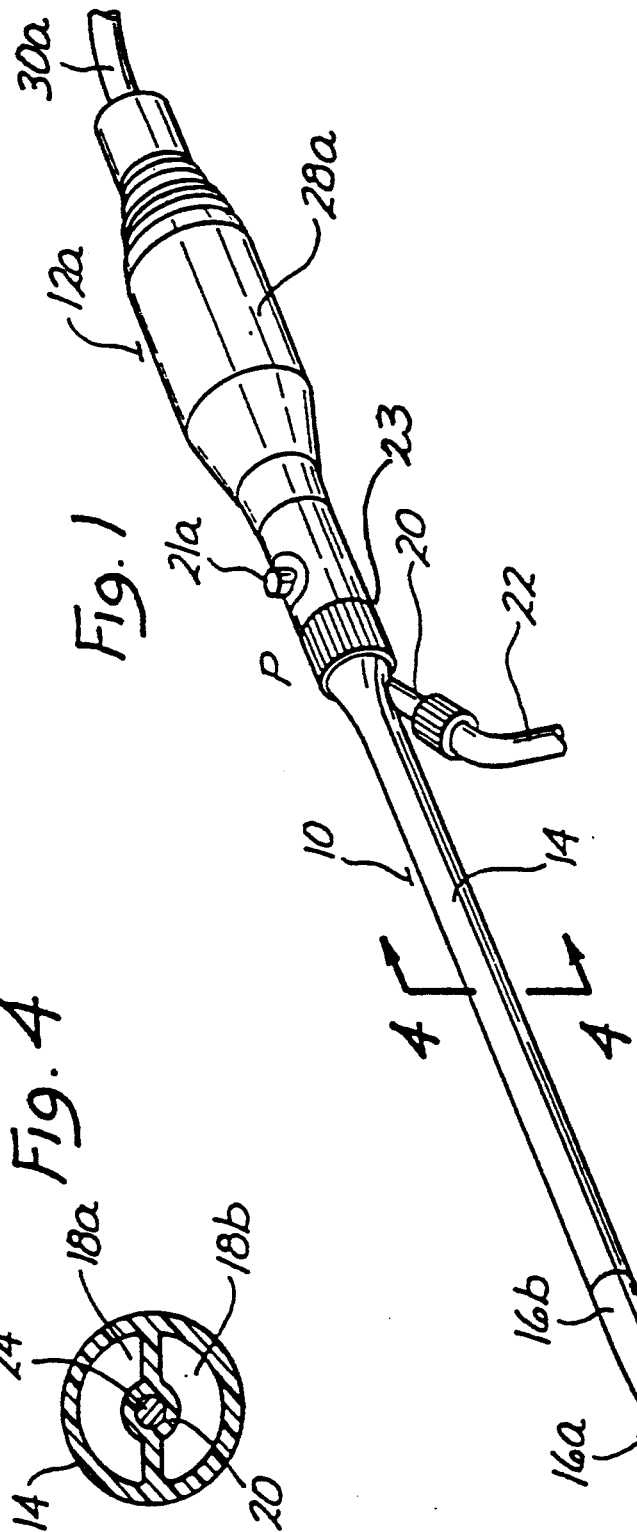
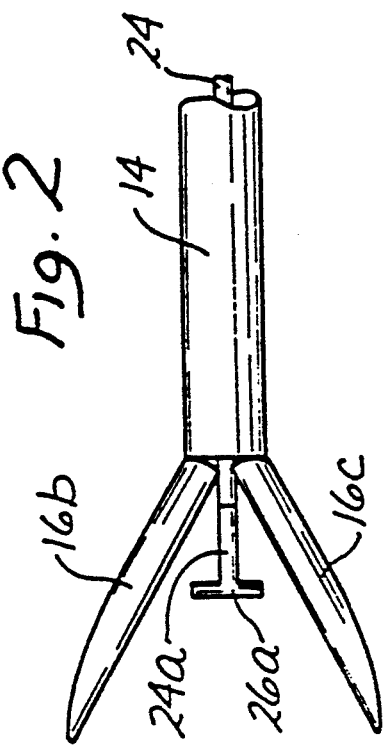
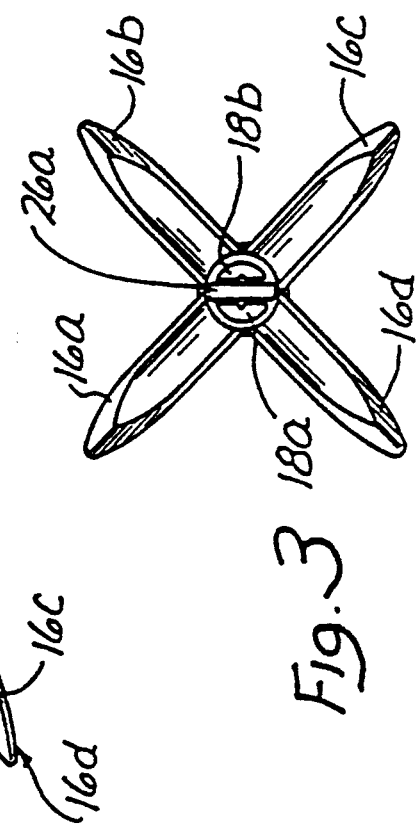
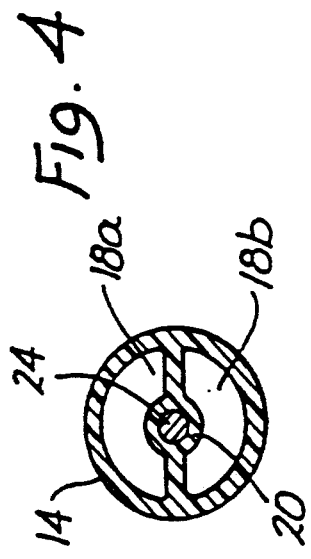

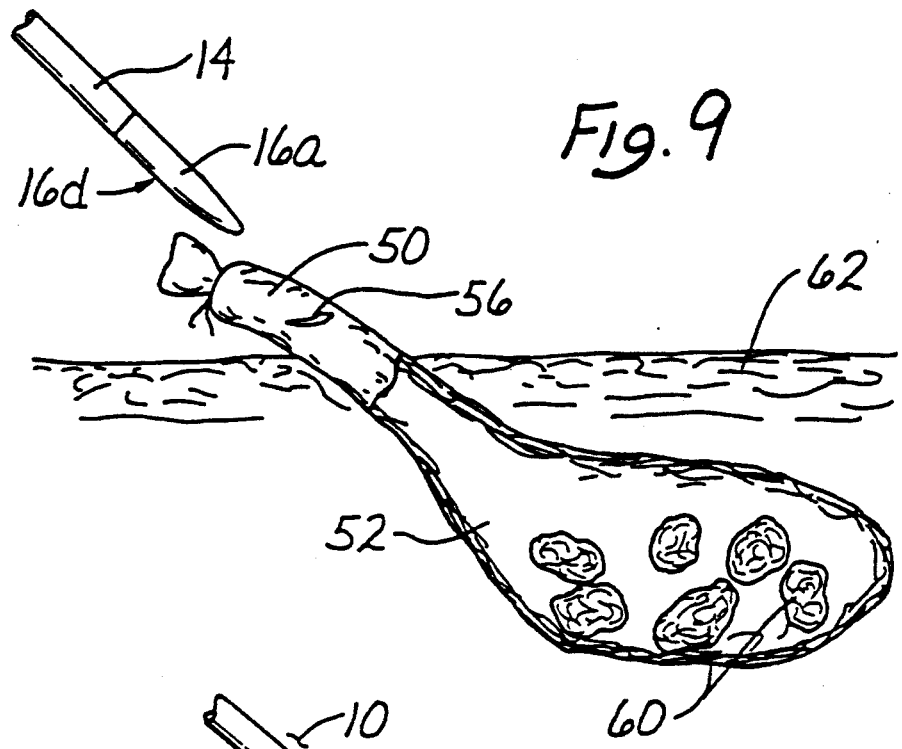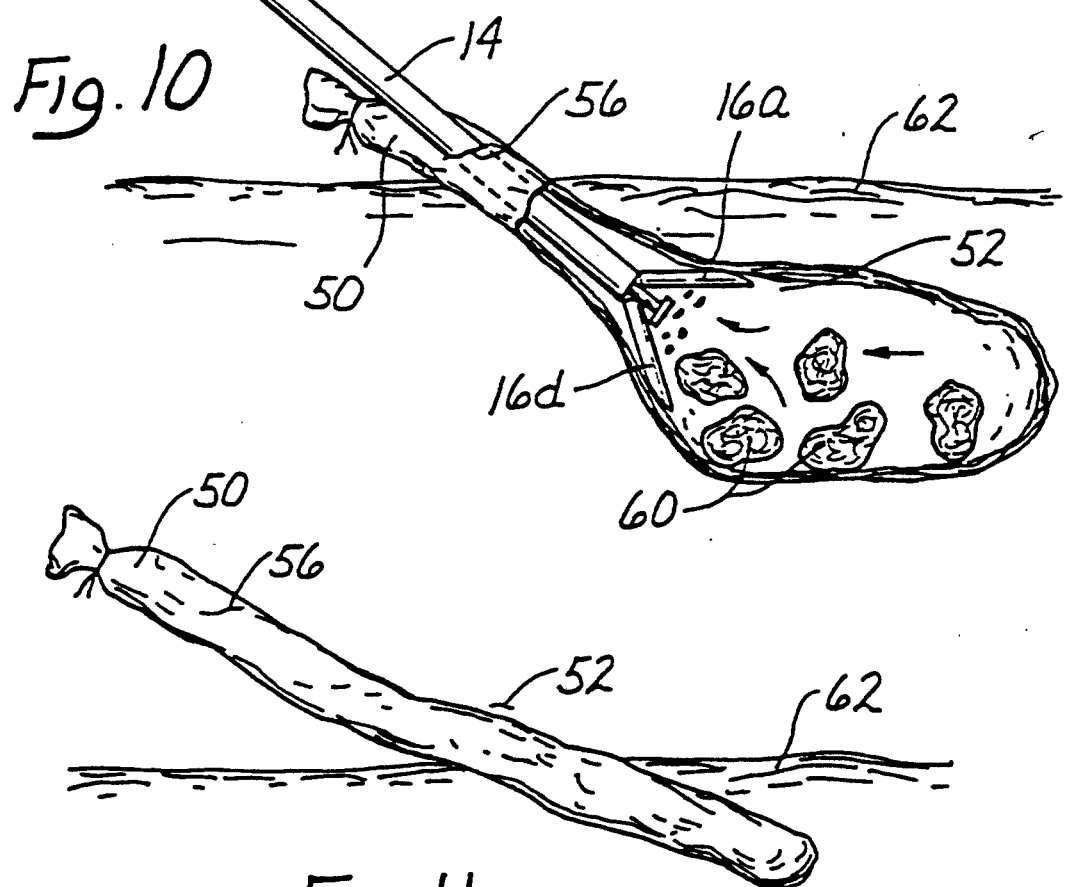

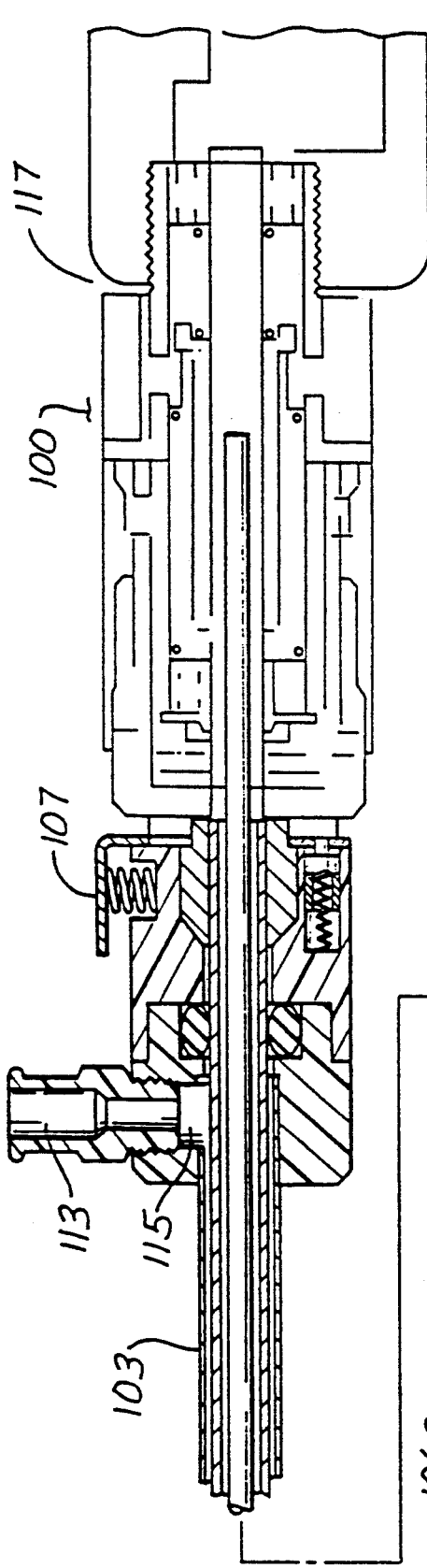
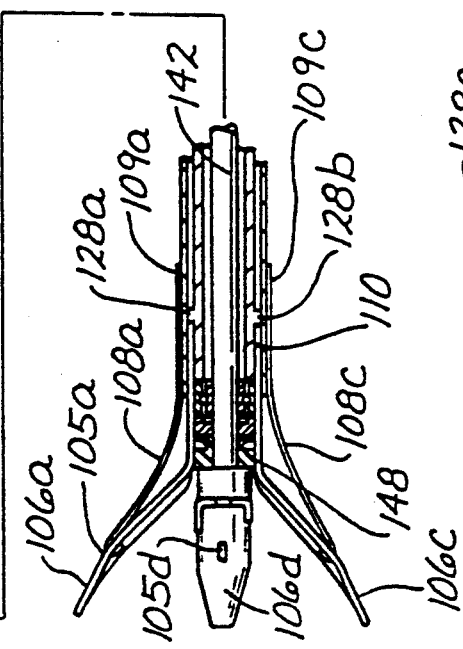
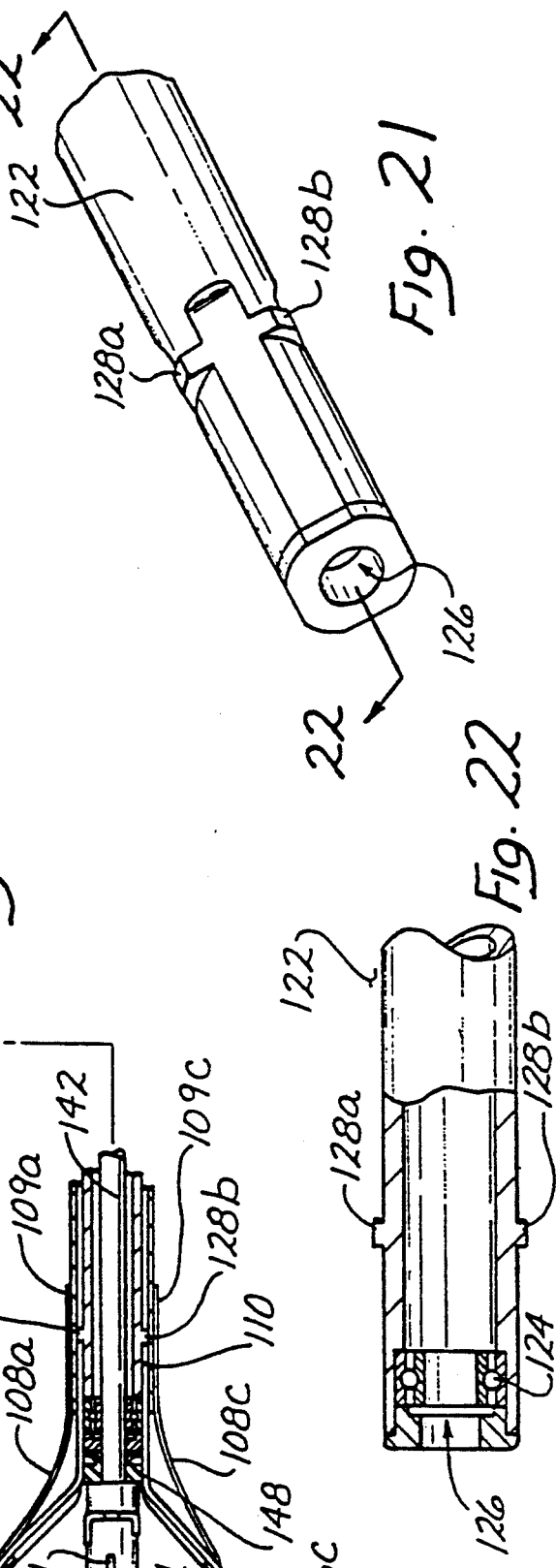

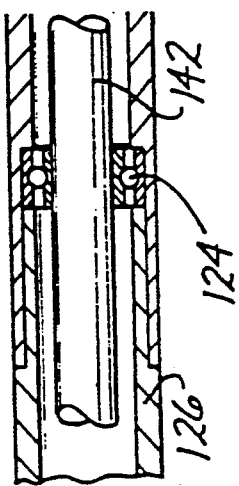
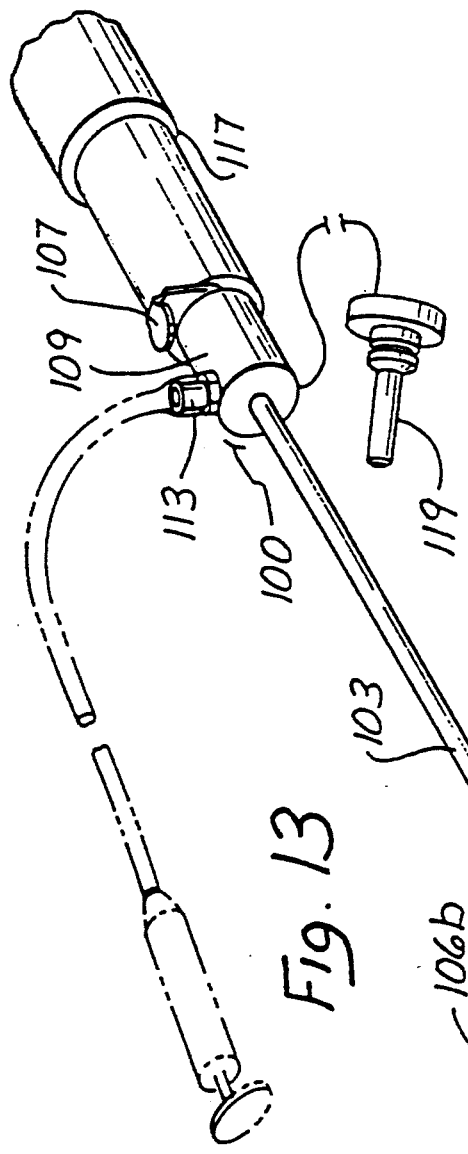
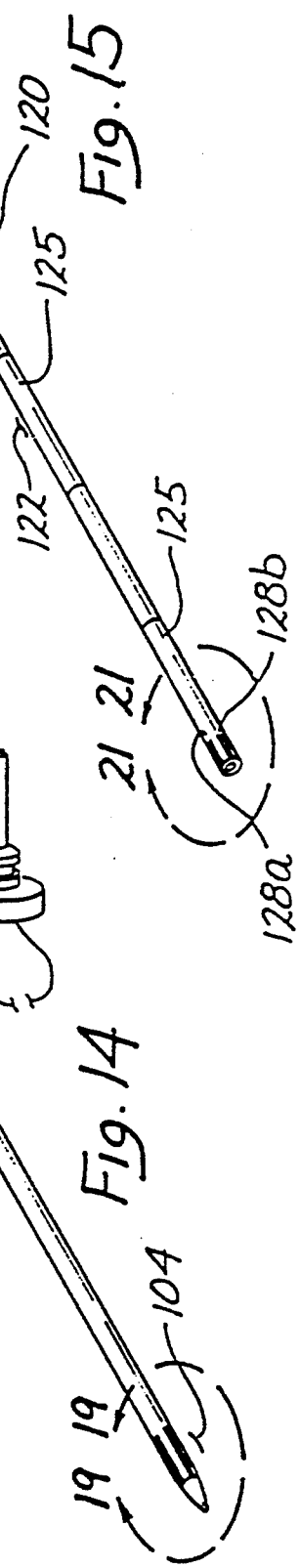

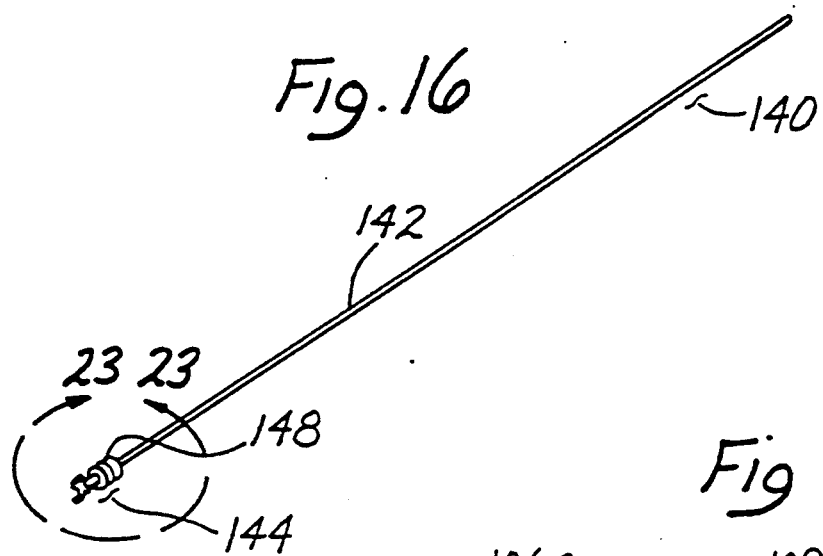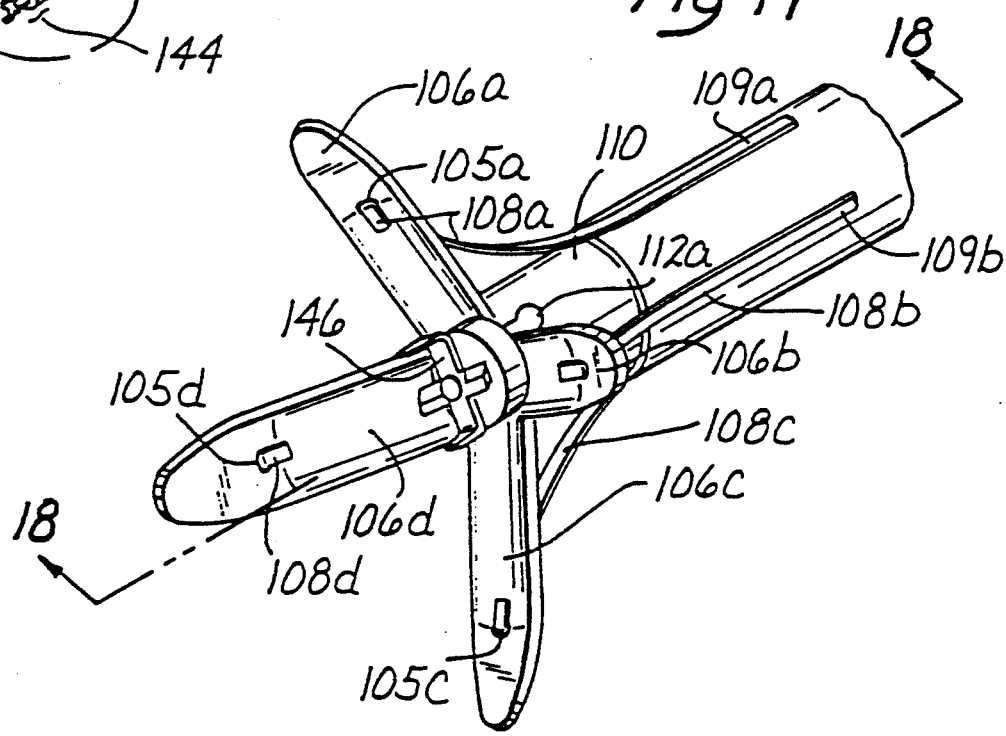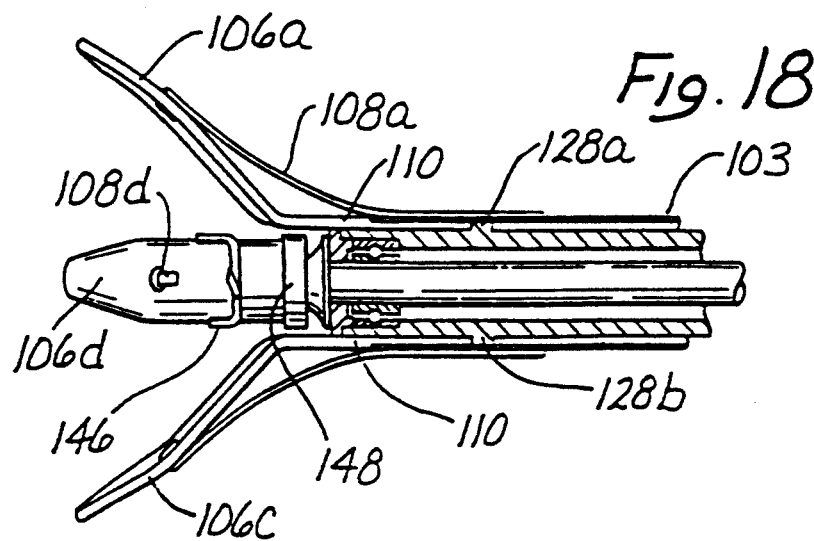

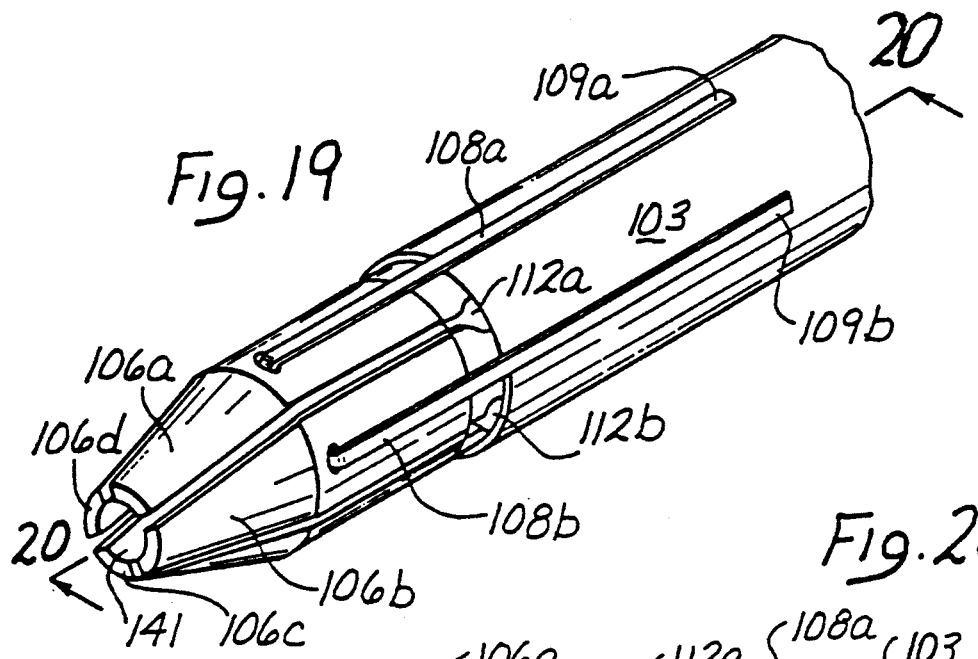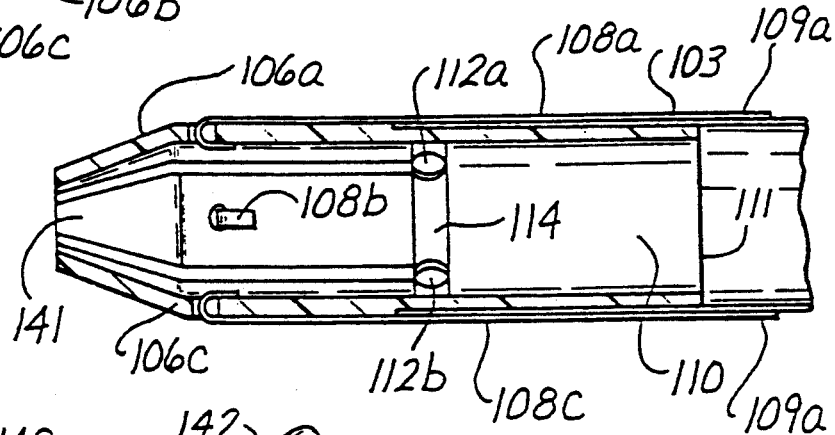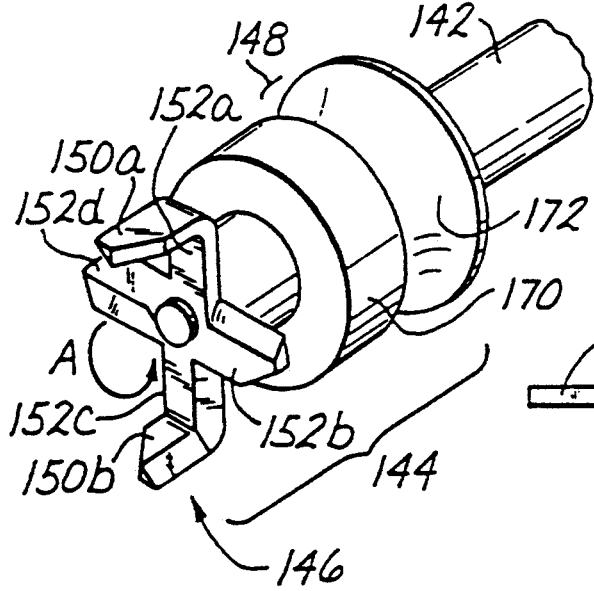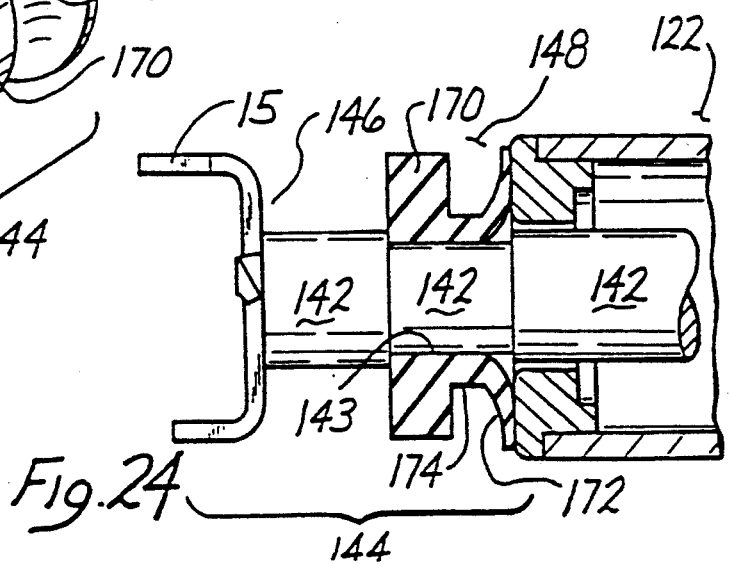

METHOD AND DEVICE FOR INTRACORPOREAL DEVICE FOR INTRACORPOREAL MORSELLING OF TISSUE AND/OR CALCULI DURING ENDOSCOPIC SURGICAL PROCEDURES

This is a continuation of copending application Ser. No. 07/639,494, filed on Jan. 9, 1991, now abandoned.

FIELD OF THE INVENTION

The present invention relates generally to medical equipment and more particularly to a device which may be inserted into the body through an existing orifice or small incision and subsequently utilized to pulverize, granulate, smash, crush, shatter, grind, tear, shred, cut, mulch, liquidize, or otherwise reduce the size of surgically excised tissues (e.g. organs, tumors, adhesions), calculi (e.g. kidney stones, bladder stones, gallstones) or other matter contained within a sac-like anatomical structure or artificial containment bag positioned within the body.

BACKGROUND OF THE INVENTION

The development of modern endoscopic instrumentation has significantly affected the manner in which many surgical procedures are performed. Indeed, many procedures which have traditionally required large surgical incisions (e.g. laparotomy) may now be performed endoscopically, by inserting an endoscopic viewing device (e.g. a laparoscope, arthroscope, bronchoscope, etc.) along with various surgical instruments through natural body openings or small incisions.

The development of modern endoscopic surgical procedures has enabled surgeons to perform major operative procedures at relatively low risk, without the need for deep muscle relaxation and with minimal blood loss and minimal post-operative discomfort.

In particular, recent advancements in laparoscopic technology have enabled surgeons to perform various intra-abdominal surgical procedures through one or more relatively small (e.g. 1 cm) laparoscopy incisions rather than through the traditional, relatively large (e.g. 5–20 cm) laparotomy incision. Although the laparoscopic technology is advanced enough to permit surgeons to laparoscopically excise various tissues and/or organs within a body cavity, (e.g. tumor removal, appendectomy, nephrectomy, cholecystectomy, etc.) the ultimate success and feasibility of such laparoscopic surgery is often confounded by the fact that the excised tissue, organ or other matter may simply be too large to be extracted from the body cavity through the relatively small (e.g. 1 cm) laparoscopy incision. In such instance, it may be necessary to enlarge the laparoscopy incision in order to effect extraction and removal of the excised tissue or other matter. Such need for enlargement of the laparoscopy incision partially negates the benefits of performing the procedure laparoscopically because enlargement of the incision is likely to cause additional post-operative discomfort and is likely to increase post-operative recovery time.

Similar problems in extracting and removing tissue or organs may be experienced in other contemporary endoscopic surgical procedures, including those which are performed through natural body openings such as the oral cavity, urethra, vagina, rectum, etc.

The present invention may be used with *any* type of endoscopic surgical procedure wherein it is desired to remove a mass of tissue or other matter from the body through a relatively small opening. Because the present invention is particularly applicable to intra-abdominal laparoscopic surgical procedures, the invention will be described herein with particular reference thereto. The making of such particular reference to laparoscopic surgical procedures shall not, however, constitute a limitation on the overall description and intended application of the present invention. In fact, in addition to intra-abdominal laparoscopic procedures, the present invention may be usable in many other types of procedures, including but not limited to transurethral removal of bladder stones, standard cholecystotomy and a modified cholecystotomy procedure known as "mini-cholecystostomy" wherein the gallbladder is, under laparoscopic guidance, displaced and sutured onto the peritoneal wall with subsequent formation of an incision or stoma through the abdominal wall, directly into the stone-containing gallbladder. Furthermore, the device of the present invention may be inserted into an organ to reduce and/or remove the contents thereof without the need for initial excision of the organ. For example, the device of the present invention may be inserted directly through the abdominal wall and into the gallbladder, urinary bladder or other sac-like structure wherein the device may be utilized to reduce the size of and/or remove aberrant material (e.g. calculi) contained within the organ, without the need for excision and removal thereof.

i. The General Methodology of Laparoscopic Surgery

Laparoscopy has, for some time, been used in the treatment of gynecologic diseases. More recently, and largely due to the development of highly efficient laser cutting and coagulation devices, laparoscopy has shown promise as a modality for performing various other general surgical procedures which had heretofore been performed through relatively large (e.g. 5–40 cm) laparotomy incisions. Indeed, frequently performed intra-abdominal surgical procedures such as cholecystectomy and appendectomy may now be approached with the laparoscope through a relatively small (e.g. 1 cm) abdominal puncture. The feasibility of performing such operations is, however, dependent upon the ability of the surgeon to extract and remove the excised tissue or organ from the body.

In accordance with standard laparoscopic technique, an inflation needle is initially inserted into the peritoneum and carbon dioxide is passed into the peritoneum to create a distended pneumoperitoneum. Thereafter, a small periumbilical incision is formed and a primary portal or trocar is inserted, through such periumbilical incision, into the distended peritoneum. The laparoscope is then inserted into the peritoneum through the primary umbilical trocar. One or more secondary trocars or accessory portals may also be inserted through one or more secondary incisions or puncture wounds formed in the abdominal wall. Such secondary trocars or accessory portals are generally used for passage of blunt forceps, cannulas and other instruments into the abdomen. After such instruments have been inserted through the accessory portals, the instruments are used to carry out the desired surgical excision and/or manipulation of organs and tissues within the abdomen while the surgeon views the operative site through the previously inserted laparoscope. The surgically excised tissue or other material which is to be removed during the surgical procedure must then be extricated from the body, preferably by extraction through one of the previously made laparoscopy portal incisions.

ii. A Specific Procedure for Laparoscopic Cholecystectomy

One particular laparoscopic surgical procedure which has become relatively common in clinical application is the "laparoscopic cholecystectomy". The laparoscopic cholecystectomy generally requires insertion of a laparoscope through the primary periumbilical portal and various forceps and other operative instruments through the secondary portals. The gallbladder is then grasped with forceps, clips are placed on the cystic artery and bile duct and the gallbladder is subsequently excised. Thereafter, the laparoscope is extracted from the primary portal and relocated to a secondary portal. Forceps are then utilized to move the gallbladder to a position adjacent the periumbilical incision and to exteriorize the neck of the gallbladder through the periumbilical incision. If possible, the entire body of the gallbladder is then extracted through the periumbilical incision. Such extraction of the gallbladder may be complicated, however, in instances where the diseased stone-containing gallbladder is too large to pass through the relatively small (e.g. 1 cm) periumbilical incision. In such instances, it is current practice to insert forceps through the exteriorized neck of the gallbladder to attempt to manually crush and remove some or all of the gallstones. Such manual crushing of the gallstones is time-consuming and may well result in perforation of the gallbladder wall. Alternatively, the surgeon may elect to enlarge the small (e.g. 1 cm) periumbilical incision in order to remove the entire body of the stone-containing gallbladder. Such enlargement of the incision is undesirable and may lead to increased post-operative discomfort.

In view of the problems associated with removing tissue, organs, or other material through a relatively small (e.g. 1 cm) laparoscopy incision, there exists a need in the art for an instrument which may be passed into the peritoneum through the standard (e.g. 1 cm) laparoscopy incision to liquidize and/or pulverize tissue or other material (e.g. gallstones) and to aspirate such liquidized/pulverized material from the body cavity.

One instrument which has previously been devised for liquidizing tissue during endoscopic surgical procedures is described in the literature. K. T. Ison, M. J. Coptcoat, A. Timoney, and J. E. A. Wickham, "The Development and Application of a Surgical Device-The Endoscopic Liquidizer and Surgical Aspirator (ELSA)", *Journal of Medical Engineering and Technology*, Vol. 13; No. 6 (November/December 1989), pg. 285-289. Such instrument is intended to be inserted through the working channel of an endoscope and incorporates an internal suction lumen along with a rotating cutting head so as to access, liquidize and aspirate tissue through a common instrument which is positioned in and inserted through the working channel of the endoscope.

Various other instruments for fragmenting, pulverizing or reducing the size of materials in situ have also been described. Examples of such instruments are found in U.S. Pat. Nos. 4,823,793 (Angulo et al.), 4,681,106 (Kensey), 4,700,705 (Kensey), 4,631,052 (Kensey), 4,002,169 (Kulper).

SUMMARY OF THE INVENTION

The present invention overcomes some or all of the shortcomings of the prior art by providing a device which is insertable through an existing body orifice or small incision and which is usable to pulverize, granulate, smash, crush, shatter, grind, tear, shred, cut, mulch, liquidize or otherwise reduce the size of surgically excised tissues, calculi or other matter contained within a sao-like anatomical structure or intracorporeally positioned artificial containment bag.

In accordance with the invention, there is provided a device comprising an elongate cutting tool having a distal cutting head such as a rotatable cutting head or impactor, disposed thereon. In one embodiment, the elongate cutting tool may optionally incorporate one or more infusion/aspiration lumens running longitudinally therethrough. In another embodiment, there may be provided an aspiration/infusion/guide cannula which is separate from the elongate cutting tool. The separate aspiration/infusion/guide cannula may be preinserted through a body opening into the intracorporeally positioned organ or containment bag and the elongate cutting tool may be inserted through the aspiration/infusion/guide cannula, operated and subsequently extracted. After the cutting tool has been employed to reduce the size of material contained with the organ or sac, such material may be aspirated through the separate aspiration/infusion/guide cannula prior to or after extraction of the cutting tool therefrom.

In accordance with one embodiment of the invention, there is provided a device comprising (a) an elongate cannula insertable through a body opening into the intracorporeally positioned organ or artificial containment bag, (b) an elongate cutting tool having a distal cutting head mounted thereon, said elongate cutting tool being insertable through the elongate cannula such that the cutting head will reside adjacent to the distal end of said cannula, and (c) drive motor which is attachable to the proximal end of the elongate cutting tool for driving the cutting head in a manner that will effect size-reducing treatment of material contained within the intracorporeally positioned organ or artificial containment sao. The cannula portion of the device may further comprise a protective assembly formed on the distal end of the elongate cannula to guard the cutting head and to prevent the cutting head from inadvertently damaging or puncturing the walls of the surrounding containment sac.

Various sizes and types of cutting heads may be provided for effecting various types of applications including, but not limited to, pulverization of kidney stones, pulverization of gallstones, pulverization of bladder stones, liquidization of excised tissues or tumors, etc.

The rotatable cutting head or impactor deployed on the elongate cutting tool may be specifically configured to create a circulatory fluid motion and/or drawing effect so as to effectively pull matter into contact with the rotating cutting head or impactor. Also, the leading edges of such rotating cutting head or impactor may be bevelled or sharpened to facilitate movement of the rotating head or impactor through the surrounding fluid and/or to enhance the matter cutting or matter breaking effect of the rotating head or impactor and/or to enhance the above-described circulatory fluid motion such that matter will be pulled or drawn into contact with the rotating head or impactor. In some embodiments, the rotating head or impactor may comprise a plurality of individual members which emanate outwardly from a central hub or shaft. Such individual members may be twisted, bent or pitched in a manner that will cause the formation of and/or enhancement of the above-described circulatory fluid motion and/or drawing effect whereby matter is pulled or drawn into contact with the rotating head or impactor.

In accordance with a further aspect of the invention, there is provided a method for removing material from an intracorporeally positioned organ or artificial containment sac. Such method comprises insertion of an elongate cutting tool into an intracorporeally positioned organ or artificial containment sac which may be partially exteriorized through a body opening or small incision to contain a quantity of material to be removed therefrom. A rotatable cutting head or impactor on the distal end of the elongate cutting tool is then rotated so as to effect size-reducing treatment of the material contained within the organ or containment sac. Following the size-reducing treatment, the cutting tool is extracted from the cannula and the material is aspirated from the sac through an aspiration cannula which is no larger than the existing body opening or small incision.

In accordance with a further aspect of the invention, there is provided a pliable, intracorporeally positionable, artificial containment sac formed of flexible material. The artificial containment sac is preferably sized and configured so as to be insertable through an existing body orifice or small incision, such as a 1 cm laparoscopy incision. In this respect, the artificial containment sac may be constructed so as to be foldable, compressible or otherwise collapsible to a small-diameter configuration which is insertable through a body orifice or small (e.g. 1 cm) laparoscopy incision. After the artificial containment sac has been inserted into the body, through the body orifice or small laparoscopy incision, it may be unfolded, decompressed or otherwise expanded to a fully operative bag-like configuration. Thereafter, a quantity of tissue or other material may be inserted into the containment sac and the sac may be positioned adjacent to, or may be partially exteriorized through, a body opening or incision. The device of the present invention or other type of cutting tool may then be inserted through the body opening or incision and into the containment sac to effect size-reducing treatment of the material contained within the organ or containment sac. In one preferred embodiment, the artificial containment sac comprises a simple bag-like structure having a single open end. A purse string, compressible closure, adhesive or other closure mechanism or closure means is provided for closing off the open end of the bag-like structure after the tissue or other material has been inserted thereinto. In another embodiment, the containment sac may comprise a bag-like body having two or more openings——e.g. one large sealable opening through which a bolus of tissue, tumor, organ or other excised material may be inserted and a second small neck opening or tube which may be at least partially exteriorized through an existing body orifice or small laparoscopy incision. The exteriorized neck portion or tube thus provides a convenient passageway through which an elongate cutting device, such as the device of the present invention, may be inserted into the sac to effect size reducing treatment (e.g. liquidization, pulverization, etc.) and subsequent aspiration of the tissue, tumor, organ or other material contained within the sac.

Further objects and advantages of the present invention will become apparent to those skilled in the art upon reading and understanding the following detailed description and the accompanying drawings.

BRIEF DESCRIPTION OF THE DRAWINGS

FIG. 1 is a perspective view of a first embodiment of the present invention.

FIG. 2 is a side elevational view of the distal portion of a first embodiment of the present invention, wherein a plurality of distal shielding members are disposed in a splayed "operative" configuration.

FIG. 3 is a distal end view of a first embodiment of the present invention wherein a plurality of distal shielding members are disposed in a splayed "operative" configuration.

FIG. 4 is a cross-sectional view through line 4—4 of FIG. 1.

FIG. 9 is a schematic showing of a first step in the operation of the device of FIGS. 1 or 5, whereby the distal end of the device of the first embodiment of the present invention is about to be inserted into a stone-containing gallbladder, the neck of the gall bladder having been exteriorized through the laparoscopy incision.

FIG. 10 is a schematic showing of a second step in the operation of the-device of FIGS. 1 or 5, whereby the distal end of the device of the first embodiment of the present invention has been inserted into a stone-containing gallbladder and the tip members thereof are disposed in a splayed or open configuration.

FIG. 11 is a schematic showing of the gallbladder of FIG. 10 after the stones contained therein have been fragmented and withdrawn such that the gall bladder may be extracted through the laparoscopy incision.

FIG. 12 is a longitudinal sectional view of a second embodiment of the present invention.

FIG. 13 is a perspective view of a second embodiment of the present invention in its fully assembled "operative" configuration including: (a) a motor/hand piece component, (b) an aspirator/guide cannula and protective cage assembly component, (c) a bearing tube disposed within the aspirator/guide cannula and protective cage assembly unit, d) a drive shaft disposed within the bearing tube and (e) an impactor head disposed on the distal end of the drive shaft.

FIG. 14 is a perspective view of the aspirator/guide cannula and protective cage assembly component of the device shown in FIG. 13.

FIG. 15 is a perspective view of the bearing tube assembly component of the device shown in FIG. 13.

FIG. 16 is a perspective view of the drive shaft and impactor head components of the device shown in FIG. 13.

FIG. 17 is an enlarged perspective view of the distal tip of the device shown in FIG. 13.

FIG. 18 is a longitudinal sectional view of the distal tip of the device shown in FIG. 13.

FIG. 19 is an enlarged view of the distal tip portion of the aspirator/guide cannula and protective cage assembly shown in FIG. 14.

FIG. 20 is a longitudinal sectional view of the distal tip portion of the aspirator/guide cannula and protective cage assembly shown in FIG. 14.

FIG. 21 is an enlarged perspective view of the distal tip portion of the bearing tube assembly component shown in FIG. 15.

FIG. 22 is a sectional view of the distal portion of the bearing tube assembly of FIG. 21.

FIG. 23 is an enlarged view of the distal tip portion of the drive shaft and the impactor head component of FIG. 16.

FIG. 24 is a longitudinal sectional view of the distal tip portion of FIG. 23 showing a preferred seal assembly which interfaces between the drive shaft component of FIG. 16 and bearing tube component of FIG. 15.

FIG. 25 is a longitudinal sectional view of a portion of the bearing tube component of FIG. 15, having the drive shaft component of FIG. 16 disposed therein.

DETAILED DESCRIPTION OF TWO PREFERRED EMBODIMENTS

The following detailed descriptions and the accompanying drawings are provided for purposes of illustrating and describing a presently preferred embodiment of the invention and are not intended to limit the scope of the invention in any way.

i. A First Embodiment

Figure 5:
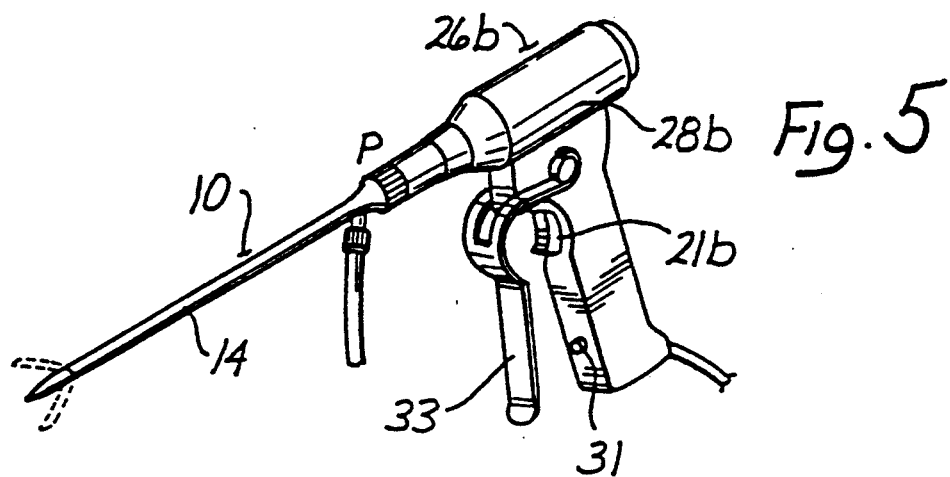
FIG. 5 is a perspective view of a first embodiment of the present invention attached to an alternate pistol-type, hand-held power drive unit.
Figure 6:
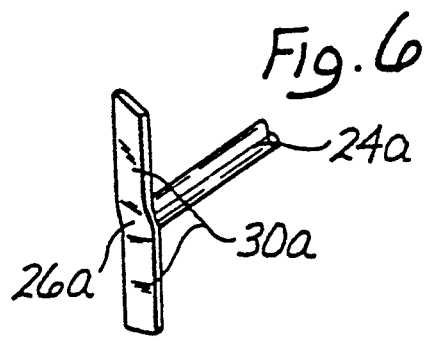
FIG. 6 is a perspective view of a first example of a rotary impacting member usable in the first embodiment of the present invention.
Figure 7:
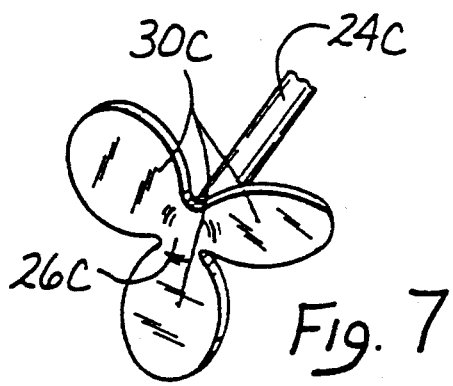
FIG. 7 is a perspective view of a second example of a rotary impacting member usable in the first embodiment of the present invention.
Figure 8:
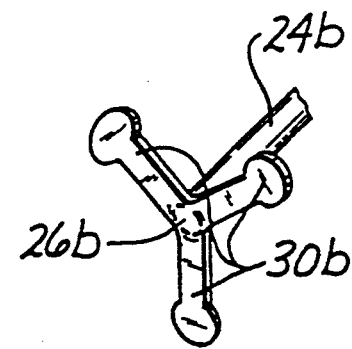
FIG. 8 is a perspective view of a third example of a rotary impacting member usable in the first embodiment of the present invention.
Figure 13A:
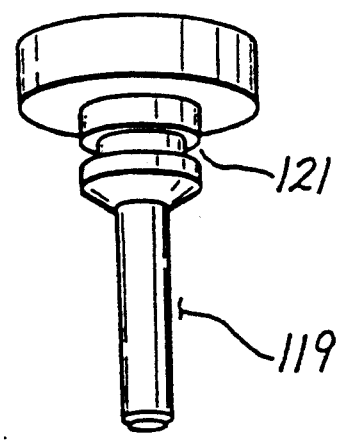
FIG. 13a is an enlarged view of the cap member attached to the device shown in FIG. 13.

Referring now to FIGS. 1–8, one presently preferred device 10 of the present invention comprises an elongate cutting and aspiration device which is detachably connectable to a hand-held drive unit 12a (FIG. 1), 12b (FIG. 5). The hand-held drive unit 12a, 12b may be formed in a generally cylindrical handle type configuration 12a or may be formed as a pistol grip type configuration 12b. Those skilled in the art will recognize that other configurations are likewise suitable.

An elongate cylindrical shaft or housing 14 has a proximal end P and a distal end D. The portion of the shaft 14 near the distal end D thereof comprises a plurality of openable and closeable tip members 16a, 16b, 16c and 16d (best shown in FIG. 3) which operate to form a protective assembly or cage around the cutting head or impactor 26a, 26b, 26c. Such tip members 16a, 16b, 16c and 16d are alternately deployable in a "closed" configuration as shown in FIG. 1 or an "open" configuration as shown in FIGS. 2 and 3.

A drive shaft 24 is rotatably disposed and supported within the elongate cylindrical housing 14. A plurality of bearings or bushings 20 may be disposed within the elongate housing 14 to support and/or facilitate rotation of the drive shaft.

Upper and lower infusion and/or aspiration lumens 18a, 18b (FIG. 4) extend longitudinally through the elongate shaft 14 of the device 10 so as to provide passageways through which fluids may be infused (distally) and/or air, fluids, debris or other matter may be aspirated (proximally) and subsequently removed or discarded. Both infusion/aspiration lumens 18a, 18b may be separately accessible through separate side arm connectors 20 or, as in the embodiment shown, both lumens 18a, 18b may terminate in a common internal collection manifold, reservoir or void formed within the proximal portion P of the elongate shaft 14. In such embodiment a single side arm connector 20 opens into such common manifold within the proximal portion of shaft 14 to provide for concomitant infusion/withdrawal through both lumens 18a, 18b. An ancillary infusion or aspiration apparatus, such as a suction tube 22, infusion tube or syringe may be attached to side arm connector 20 to effect the desired infusion or aspiration through lumens 18a, 18b.

When it is desired to aspirate material proximally through the lumens 18a, 18b the tube 22 may comprise a suction or vacuum tube attached to standard wall suction, a dedicated suction pump or other suction means whereby the operator may apply continuous and/or intermittent suction through the lumens 18a and/or 18b.

Additionally, it will be appreciated that the device may be provided with both a fluid supply lumen 18a or 18b and a separate aspiration lumen 18a or 18b, so that fluid may be infused (distally) through one lumen into the intracorporeal containment sac (e.g. natural organ or artificial sac) while fluid/stone fragments/debris or other material is simultaneously or intermittently aspirated (proximally) through a separate lumen. Such concomitant infusion and aspiration may effect a lavage-like washing of the interior of the organ or sac into which the device 10 has been inserted so as to efficiently remove or extract fluid, debris, stone fragments or other matter therefrom.

While it is preferable to incorporate one or more infusion and/or aspiration lumens 18a, 18b within the elongate shaft 14 as shown, it will be appreciated that such lumens 18a, 18b are optional features of the device 10 and may be eliminated altogether.

Power unit 12a, 12b may be operatively connected to the proximal end P of the elongate shaft 14 by any feasible mechanical, magnetic or other connection means by which the power unit 12a, 12b may engage and rotatably drive shaft 24 so as to cause resultant rotation of the impactor head 26a, 26b, 26c. The power unit 12a, 12b comprises an outer housing 28a, 28b wherein a small electric or pneumatic motor is mounted. The electric or pneumatic motor is sized and adapted to drive the drive shaft at a fixed speed or may be capable of driving the drive shaft at variable speeds as desired. The electric or pneumatic motor (not shown) is connected to a drive assembly which mechanically, magnetically, or by other means, drives shaft 24a (FIG. 2 and FIG. 6), 24b (FIG. 8), 24c (FIG. 7) in a rotary fashion. An electrical power cord or pneumatic pressure line 30a, 30b is connected to the power unit 12a, 12b so as to provide the necessary pneumatic or electrical power to the motor disposed within housings 28a, 28b and on/off or variable speed control trigger 21a, 21b actuates the motor.

The "pistol grip" power unit 12b shown in FIG. 5 incorporates an "enable switch" 31 which must be closed in order for the motor disposed within housing 28b to be actuated. As shown, the hand grip 33 may be pulled back to depress enable switch 31, thereby closing the enable switch 31 and allowing the motor to be actuated upon depression of trigger 21b. If the enable switch 31 is not closed, compression of trigger 21b will be ineffectual, and will not result in actuation of the motor.

In the first embodiment, the tip members 16a, 16b, 16c, and 16d are hinge mounted or otherwise pivotally connected to the distal end D of the elongate shaft 14 so as to be alternately deployable in a closed configuration (FIG. 1) or an open configuration (FIGS. 2 and 3). When in the closed configuration, the outer surfaces of the tip members 16a, 16b, 16c and 16d form a smooth, cylindrical surface which is generally continuous with and emanates forward to the outer surface of the elongate shaft 14 so as to permit smooth, unencumbered introduction of the distal portion of the elongate shaft 14 into the gallbladder or other sac through a small (e.g. 1 cm) incision or opening.

When the tip members 16a, 16b, 16c, 16d are deployed in their "open" or splayed configuration they will form a protective cage around the rotating head or impactor 26a, 26b, 26c to prevent the head or impactor from damaging or puncturing a surrounding organ or artificial containment sac. Also, it is preferable that the distal tip members 16a, 16b, 16c, 16d be configured such that, when deployed in said open or splayed configuration, will form an abutment means which, upon attempted proximal withdrawal of the device, will abut against the neck of the organ or sac and/or the body wall so as to prevent the device from being accidentally withdrawn during use and also to maintain proper positioning of the cutting head (i.e. the operator may purposely withdraw the instrument to a point where the open tip members 16a–16d abut against the body wall thereby ensuring that the cutting head is at or near the top of the organ or artificial sac and not near the fundus or bottom wall thereof as may result in damage or puncture of the organ or artificial sac.

The embodiment of the invention shown in FIGS. 1 and 5 may incorporate any suitable means for controlling the opening and closing of the distal tip members 16a–16d. For example, in the embodiment shown in FIG. 1 wherein the generally cylindrical motor drive hand piece 12a is employed, a rotatable dial member 23 may be attached to one or more advanceable/retractable members 15 which extend through the elongate shaft 14 and are attached at their distal ends to the tip members 16a–16d. The advanceable/retractable members 15 are connected to the dial member 23 by gears or other mechanical transfer arrangement such that turning of the dial member 23 in one direction (e.g. clockwise) will cause proximally directed advancement of the members 15, thereby forcing the distal end pieces 16a–16d to pivot on hinged connections to their open or splayed configuration shown in FIGS. 2 and 3. Thereafter, turning of the dial 23 in its opposite direction (e.g. counter-clockwise) will cause the members 15 to retract in a distal direction, thereby pulling the distal end pieces 16a–16d back to their original closed configuration as shown in FIG. 1.

Alternately, in embodiments which incorporate a pistol grip-type hand piece 12b, a separate protective assembly trigger 33 may be employed. Such trigger 33 may be connected by way of rack and pinion gears or other mechanical interconnection to one or more members 15 extending longitudinally through the elongate shaft 14 of the device such that, when the trigger 33 is retracted against the hand piece the members 15 will advance in the distal direction causing the distal end pieces to open into their splayed configuration. Alternately, when the trigger 33 is allowed to return to its resting position, as shown, the member(s) 15 will retract within the elongate shaft 14 in a proximal direction, thereby allowing the distal end member 16a–16d to return to their closed position.

As an alternative to the advanceable/retractable members 15 shown, the hand-actuatable dial 23 or trigger 33 may be operatively connected to any other suitable type of mechanism capable of opening and closing the tip members 16a, 16b, 16c and 16d. Such other types of mechanism may include a cable and pulley system having cable(s) running longitudinally through the device 10 and attached to the dial 23 or trigger 33 to effectuate alternate opening and closing of the tip members 16a, 16b, 16c and 16d. Those skilled in the art will recognize that various other mechanical means for effecting actuation of the tip members 16a–16d are also possible.

As an alternative to mechanical means for opening/closing the tip members 16a–16d, one or more wires or members made of a shape memory alloy may be disposed within the device. Such shape memory alloys have the ability to lengthen, bend, or otherwise distort in shape upon undergoing heating above a specific transition temperature. Accordingly, strands or ribbons of these materials may be positioned within the distal tip members 16a–16d, 106a–106d or wires or strands of these shape memory alloys may extend fully through the longitudinal body 14 of the instrument (or the cannula 103 of the hereinafter described second embodiment) such that, when electrical energy, sound energy or other means are utilized to raise the temperature of the shape memory alloy, the alloy will distort or change shape, causing the distal tip members 16a–16d, 106a–106d to move to their "open" configuration. Thereafter, when the energy source is discontinued, the shape memory alloy elements will cool to a temperature below their transition temperature and will return to their original shape, thereby causing said distal tip members 16a–16d or 106a–106d to return to their original "closed" configuration.

It is desirable that the enable feature, such as the enable switch 31 shown on the pistol hand grip embodiment 12b be interrelated to the protective assembly opening and closing mechanism such that the device will only be enabled when the protective assembly is opened. Thus, as shown in FIG. 5, the trigger 33 of the pistol hand grip assembly 12b will only depress the enable switch 31 when it is in a position whereby the protective assembly is "open". When the trigger 33 is returned to its resting position so as to return the protective assembly to its "closed" position, the enable switch 31 will not be depressed and the rotatable cutting head or impactor 26a, 26b, 26c will not undergo rotation even if the trigger 21b is accidently depressed. Alternately, depression of the enable switch may not actually enable the trigger unless the protective assembly is "open". Various electrical interlock systems are well known for preventing actuation of the cutting head when the protective assembly is in its "closed" position and such interlock systems may be incorporated into either embodiment of the present invention.

Various types of rotary cutting heads or impactors 26a, 26b, 26c may be connected to the distal end of drive shaft 24. It is preferable that the cutting heads or impactors 26a, 26b, 26c comprise a plurality of flanges or wings 30a, 30b, 30c which extend outwardly from a central shaft portion 24a, 24b, 24c. Such flanges or wings 30a, 30b, 30c are preferably formed with some angular pitch as shown to create a proximally directed flow or "pull" of the gallbladder contents toward the proximal end of the device in the manner of a fan blade or propeller. This pulling action facilitates efficient shredding, cutting, pulverization, breakage, liquidization or other size-reducing treatment of material contained within the intracorporeal containment sac by pulling such material into contact with the rotating cutting head or impactor 26a, 26b or 26c.

ii. Operation of the First Embodiment

Referring now to FIGS. 9-11, this first embodiment of the present invention may be utilized to effect size reduction on any tissue or other material contained within an intracorporeal containment sac (e.g. a natural organ or an intracorporeally positioned artificial sac).

In one particular procedure, the device 10 may be utilized to pulverize or fragment gallstones, within a gallbladder, after the gallbladder has been excised by a laparoscopic excision technique and, after the neck or other portion of the gallbladder has been partially exteriorized through the laparoscopy incision.

In accordance with the standard laparoscopic cholecystectomy operative technique, a laparoscope is inserted through a small (e.g. 1 cm) abdominal incision or primary portal and is advanced to a point whereat the gallbladder 52 can be visualized and accessed through the laparoscope. The gallbladder 52 is accessed by instruments inserted into the peritoneum through one or more "secondary" portals. The surgeon then utilizes the inserted instruments to apply ligatures 54 or clips to blood vessels and to the cystic duct neck 50 of the gallbladder 52 and to thereafter excise the gallbladder 52. The laparoscope is then removed from the primary portal and forceps are inserted in its place. The excised gallbladder 52 is then grasped by forceps introduced through the primary portal and manipulated such that the portal trocar is removed and the ligated neck 50 of the gallbladder 52 becomes exteriorized through the tract of the laparoscopy incision (FIG. 9). Thereafter, a small in incision 56 is formed within the exteriorized neck 50 of the gallbladder 52 and the distal portion D of the elongate shaft 14 is inserted through the incision 56. The distal portion D of the elongate shaft 14 is then advanced toward the fundus of the gallbladder, to a point where the distal portion D of the elongate shaft 14 lies within the cavernous stone-containing body of the gallbladder 52. At that point, the surgeon may trigger an actuating dial member 23 or trigger mechanism 33 to cause the tip members 16a, 16b, 16c, 16d to move to their open or splayed configuration (FIG. 10). In such "open" configuration the tip members 16a, 16b, 16c and 16d form a protective cage around the rotary cutting head or impactor 26a, 26b, 26c such that the cutting head or impactor 26a will be substantially prevented from contacting the wall of the gallbladder or other intracorporeal containment sac 52, thereby minimizing the likelihood of inadvertent traumatization or penetration of the gallbladder wall or intracorporeal containment sac.

After the tip members 16a, 16b, 16c and 16d have been moved to their "open" configuration. The surgeon then proximally retracts the device 10 until the open tip members 16a-i6d abut against the neck or top of the containment sac 52 or against the body wall 62, thereby enabling the surgeon to accurately gauge the depth of the cutting head or impactor 26a, 26b, 26c. Thereafter, any air present in the gallbladder is purged from the gallbladder and liquid (e.g. saline solution) is infused via infusion/aspiration port 20 to fill and fully distend the gallbladder 52. The surgeon will then depress the trigger button 21a, 21b to cause the shaft 24a, 24b, 24c to rotate, thereby resulting in rotary movement of the cutting head or impactor 26a, 26b, 26c. By such rotary movement, the flanges 30a, 30b, 30c of the impactor 26a, 26b, 26c which may be pitched or angled, will cause surrounding gallstones, bile or other material to be pulled into contact with the cutting head or impactor 26a, 26b, 26c, as denoted by the arrows on FIG. 10. The cutting head or impactor 26a, 26b, 26c will strike and pulverize the gallstones 60 which are contained within the sac-like gallbladder 52.

The attendant suction source and/or fluid supply source may be utilized to intermittently or continuously infuse fluid in a distal direction and/or to purge air and/or to withdraw fluid and stone fragments in a proximal direction, through either or both of the lumens 18a, 18b. At the end of the procedure, it is preferable that all of the gallstones 60 be fully pulverized and that the majority of the gallbladder 52 contents be aspirated therefrom, so as to render the gallbladder a collapsed structure as shown in FIG. 11. Thereafter, the device 10 is withdrawn from the neck 50 of the gallbladder 52 and the organ is simply extracted through the laparoscopy incision. Thereafter, the small laparoscopy incision is closed by standard suturing or other closure technique if required, and the patient is permitted to recover.

iii. A Second Embodiment

A second embodiment of the present invention is shown in FIGS. 12-27. This second embodiment of the invention differs from the above-described first embodiment in that a separate aspirator/guide cannula is initially inserted into the organ or tissue-containing bag. A separate cutting tool is then advanced through the aspirator/guide cannula, and may be employed to cut or pulverize the material (e.g. tissue, calculi or other material) desired to be treated. Thereafter, the cutting tool is retracted from the aspirator/guide cannula. The previously pulverized or liquidized material is then aspirated through the aspirator/guide cannula and the bag or organ is then extracted.

An example of this second embodiment of the present invention is the device 100 shown in FIGS. 12-27. Such device 100 comprises an aspirator/guide cannula component 102. Such aspirator/guide cannula component 102 comprises an elongate tube or cannula body 103 having a hub 109 and latch mechanism 107 formed on the proximal end thereof.

A protective cage assembly 104 is disposed on the distal tip of cannula 103. A cap 119 is attached to the aspirator/guide cannula 102 by a tether and is insertable into the proximal end opening of hub 109 so as to plug or cap the proximal opening into the lumen of the cannula 103. Portions of latch mechanism 107 seat within groove 121 to lock the cap 119 in place. When it is desired to remove cap 119 the latch 107 is depressed, causing the latch 107 to disengage groove 121, thereby allowing manual removal of cap 119.

The protective cage assembly 104 disposed on the distal end of the cannula body 103 comprises a plurality of distal tip members 106a, 106b, 106c and 106d. Such distal tip members 106a-106d may be made of any acceptable material, including polyethylene, polypropylene or other plastics. Spring members 108a, 108b, 108c and 108d (best shown in FIGS. 12, 17, 18 and 19) are affixed to the outer surface of the tube or cannula 103 and are separately attached at their distal ends to each of the distal tip members 106a-106d respectively, so as to spring-bias member 106A-106D to their closed position. In the embodiment shown, small slots or apertures 105a-105d are formed in each of the distal tip members 106a-106d and the tips of spring members 108a-108d are inserted through slots 105a-105d and crimped over so as to be firmly retained therein and to thereby remain firmly attached to the tip members 106a-106d.

The tip members 106a-106d are pivotally joined to and are continuous with an annular insert body 110. The annular insert body 110 inserts into the distal tip of the tubular cannula 103. In devices wherein the distal tip members 106a-106d and the annular insert body 110 are formed of continuous plastic material (e.g. polyethylene, polypropylene, etc.) the desired pivotal or bending movement of the distal tip members 106a-106d relative to the annular insert body 110 may be achieved by forming cutout regions 112a, 112b near the base of each distal tip member 106a-106d and/or forming a weakened grooved or scored region 114 immediately adjacent the point whereat it is desired to have the distal tip member 106a-106d bend or pivot outwardly relative to the stationary annular insert body 110.

The annular insert body 110 remains slidably disposed within the distal portion of the tubular cannula 103 such that, when an elongate cutting tool is inserted through the tubular cannula 103, it will engage and/or push against the annular body 110, causing the annular body 110 to slide forward relative to the tubular cannula 103. Such forward movement of the annular insert body 110 will cause the distal tip members 106a-106d to pivot or splay outwardly as shown in FIGS. 17-18. Thus, so long as the cutting device remains inserted through the cannula 103, the distal tip members 106a-106d will form a protective cage around the cutting device to prevent or minimize the likelihood of inadvertent puncture of the surrounding containment sac or organ.

It will be appreciated that the opening and closing of the protective assembly distal tip members 106a-106d may, alternatively, be effected and controlled by various other mechanical or physical means including, but not limited to, the inclusion of distally advanceable/proximally retractable control rods or members and/or the use of thermally alterable shape memory alloys as described above with respect to the first embodiment.

Additionally, it is preferably that the distal tip members be configured such that, when in their open or splayed position, they will form an abutment surface to prevent inadvertent withdrawal of the device and to provide a convenient means of ensuring that the device is properly positioned near the top of the organ or artificial containment sac. This aspect of the protective cage is fully described with respect to the first embodiment (above).

With particular reference to FIGS. 15, 21, 22 and 25, the bearing sleeve 120 comprises an bearing sleeve 122 having a plurality of bushings or bearings 124 (see FIG. 22) mounted within the bearing sleeve 122 at spaced intervals therealong to prevent shaft vibration and to facilitate rotational movement of the drive shaft within the lumen of the bearing sleeve 122. As shown, to facilitate placement of the bushings or bearings and construction of the bearing sleeve 122, the bearing sleeve 122 may consist of a plurality of individual tubular segments 126 assembled in end-to-end fashion with the bushings or bearings 124 (see FIG. 22) being captured and held in place, therebetween. The bushings or bearings 124 (see FIG. 22) may comprise ball bearings, roller or rod-type bearings, pin and needle-type bearings or any other rotatable bearing assembly or nonrotatable bushing capable of facilitating the desired rotational movement of the drive shaft 142. In many applications, it is desirable that the bearings 124 (see FIG. 22) be capable of withstanding and maintaining a preferred drive shaft 142 rotational speed in excess of about 20,000 rpm preferably within the range of 20,000-100,000 rpm, and, in certain applications such as pulverization of gallstones, preferably approximately 80,000 rpm during operation of the device.

The distal tip of the bearing sleeve 122, as shown in FIG. 21, is formed to incorporate a distal opening 126 through which the cutting head or impactor head may emerge and a plurality of abutment shoulders 128a, 128b or a continuous annular ridge or ring formed on the outer surface thereof. Abutment shoulders 128a, 128b or the continuous ridge or ring will serve to abut against the proximal edge 111 of the insert body 110 so as to cause forward advancement of the insert body 110 (shown in FIG. 20), with resultant outward pivotal splaying of the distal tip members 106a-106d. A proximal hub 130 (FIG. 15) is formed on the proximal end of the bearing tube assembly 120. Such proximal hub 130 is sized and configured to nest within the proximal hub 109 of the aspirator/guide cannula 102 when the cutting tool portion of the device (i.e. the bearing sleeve 122 with drive shaft 140 and cutting head 144 disposed therein) is inserted through the aspirator/guide cannula assembly 102.

In embodiments wherein the plural abutment shoulders 128a, 128b are replaced by a continuous annular ridge or ring, such annular ridge or ring may fully block fluid flow through the space between the inner surface of cannula 103 and the outer surface of the bearing sleeve 122. In such embodiment, it will be desirable to form one or more fluid outflow apertures through the wall of the cannula 103 to allow fluid to flow in and/or out of the space existing between the inner surface of cannula 103 and the outer surface of bearing sleeve 122. Such aperture(s) located will be fully or partially proximal to the location of the annular ring or ridge to allow fluid (e.g. air or liquid) being aspirated or infused through the cannula 103 to pass in and/or out of the cannula lumen even though the elongate cutting device is fully inserted therein and the continuous annular ridge or ring may be blocking the flow of fluid into or out of the distal end of the cannula 103.

The drive shaft/impactor head assembly 140 comprises an elongate metal rod or shaft 142 having an impactor head assembly 144 disposed on the distal end thereof. The impactor head assembly 144 comprises a rotating impactor 146 and a seal 148, both of which are affixed to the distal portion of the shaft 142. The rotatable cutting head or impactor 146 may be formed in any configuration which is capable of serving the desired tissue liquidization and/or matter pulverizing function of the device. In fact, the shaped configuration and design of the impactor 146 may be varied depending on the particular application. For example, in applications wherein it is desired to liquidize an excised tumor or other tissue, the impactor may be designed for efficient cutting and liquidization of such tumor or other tissue. On the other hand, in applications wherein it is desired to pulverize gallstones, kidney stones or other hard material, it may be desired to form the cutting head or impactor 146 in a manner that will maximize its efficiency in pulverization of hard material.

As shown in FIGS. 23-24, one preferred cutting head or impactor 146 comprises a cross-shaped structure having first, second, third and fourth lateral members 152a, 152b, 152c and 152d formed in a cross with first and second struts 150a, 150b extending forwardly from two (2) of the lateral members 152a, 152c which form the cross-shaped structure. Also, the leading edges of two (2) of the blades 152b, 152d and the leading edges of the forwardly extending struts 150a, 150b are bevelled or sharpened such that, when the cutting head or impactor 146 rotates in the direction of arrow A will enhance the formation of circulatory flow or movement within the surrounding liquid. The bevelled or sharpened leading edge of the forwardly extending struts 150a, 150b may also enhance the pulverization, granulation, smashing, crushing, shattering, grinding, tearing, shredding, cutting, mulching, liquidization or other size-reducing treatment of the matter contained in the sac 200. The creation of such circulating current, movement or pull of material into the impactor 146 causes the material (e.g. tissue, gallstones, etc.) contained within the sao or organ 200 to undergo complete size-reducing treatment while the device 10, 100 is held still, in a single position within the sac or organ.

The size and configuration of the cutting head or impactor 146 may be varied depending on the consistency of the material to be treated and the other variables associated with the particular application in which the invention is being used. Typically, the cutting head or impactor 146 will be slightly smaller in cross-dimension than the internal diameter of the cannula 103 so as to permit ease of insertion and passage of the cutting tool through the cannula. In the preferred embodiment shown, the outside diameter of the cannula will generally be less than 1 cm, and preferably about 0.7 cm, so as to permit passage of the cannula through the neck portion of an organ or containment sac which has been exteriorized through a standard (e.g. 1 cm) laparoscopy incision. The cross-dimension of the cutting head or impactor 146 and/or bearing sleeve 122 is at least slightly less than the inside diameter of the cannula 103 (e.g. 0.5-0.9 cm) to facilitate insertion therethrough.

The seal 148 is seated within an annular detent or groove 143 formed on the outer surface of the shaft 142, thereby preventing undesired longitudinal slippage or movement of the seal 148. It is desired that the seal 148 forms a gas and liquid tight seal against the open end of the bearing sleeve 122. It is desirable that the gas and liquid tight seal 148 be capable of maintaining such gas and liquid tight seal after repeated high speed rotations at approximately 80,000 rpm or above.

A presently preferred seal which has been found to be usable in this application is that which is commercially available under the trade designation "V-RING" from Forsheda Shaft Seal Corporation, 26820 Fargo Avenue, Cleveland, Ohio 44146. As shown, this presently preferred shaft seal 148 is made of elastomeric material and comprises a body portion 170 and a conical lip portion 172, the conical lip portion 172 being continual with the body portion 170 and having a resilient region or "hinge" 174 formed therebetween. The conical lip portion 172 of seal 148 seats against the counter-facing surface of the distal end of the bearing tube assembly 120, as shown. The body portion 170 is seated within the annular groove formed on the outside of the shaft 142 and holds the conical lip portion 172 in contact with the distal end of the bearing tube assembly 120, thereby forming a gas and liquid tight seal therebetween.

When in its fully assembled operative configuration, the proximal end of the shaft 142 inserts within and is rotatably engaged by the drive assembly of the motor/hand piece 117. Also, latch 107 will engage a shoulder or groove formed on enlarged portion 131 of bearing tube assembly 120 to lock the bearing tube assembly and attendant components of the elongate cutting device in the fully inserted and fully advanced position relative to the aspirator/guide cannula 102. Subsequently, when it is desired to extract and remove the cutting device from the aspirator/guide cannula 102, the latch 107 is depressed causing the latch to disengage the shoulder of the enlarged portion 131, thus allowing the bearing tube assembly 120 (and the other components attached thereto) to be extracted as a unit from the aspirator/guide cannula 103. When the elongate cutting device is operatively inserted through the cannula 103, the distal end of the shaft 142, having the cutting head or impactor 146 thereon, is adjacent the distal end of the cannula. In the embodiment shown, the cutting head or impactor 146 protrudes slightly beyond the distal end of the cannula 103 such that the impactor 146 is amidst and within the distal tip members 106a-106d.

iv. Operation of the Second Embodiment

Figure 26:
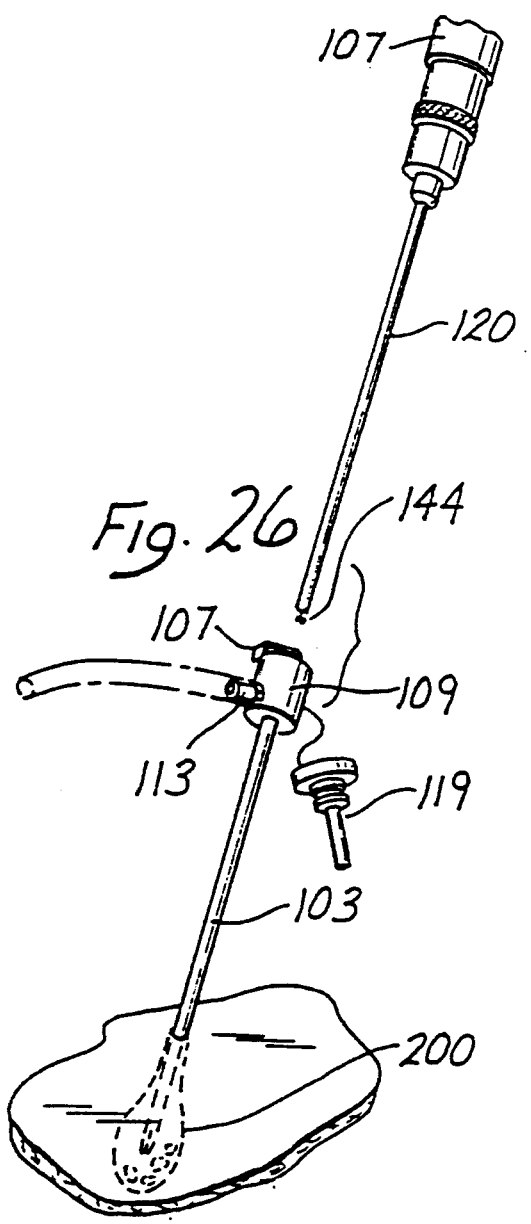
FIG. 26 is a schematic showing of a first step in the operation of the device of FIG. 13, whereby the aspirator/guide cannula and protective cage assembly has been inserted into a stone-containing gallbladder.
Figure 27:
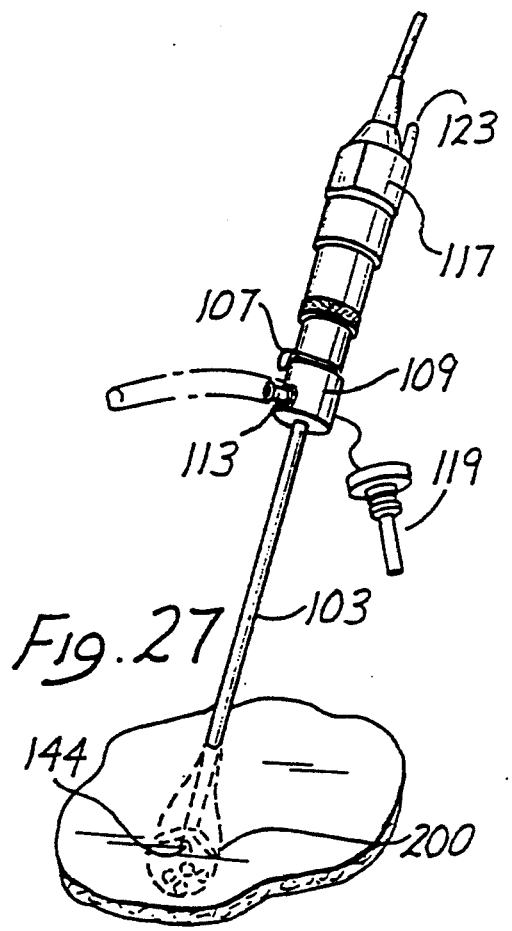
FIG. 27 is a schematic representation of a second step in the operation of the device of FIG. 13 whereby the bearing tube, drive shaft and impactor head assemblies have been advanced through the aspirator/guide cannula, causing the protective cage assembly to open to a splayed "operative" configuration.

After the organ or other bag-like structure 200 containing the tissue or other material to be treated has been partially exteriorized from the body or positioned adjacent an incision or body opening, the distal portion of the aspiration/guide cannula 102 is inserted into the intracorporeal containment sac (e.g. a sac-like organ or artificial sac) as shown in FIG. 26. The cap member 119 is initially inserted within the open proximal end of the hub 109 so as to seal such open end. A quantity of saline solution or other fluid may be introduced by way of a syringe through side arm 113. Such saline or other fluid will flow downwardly through the tubular cannula 103 where it can exit through opening 141 and will fill the intracorporeal containment sac (e.g. organ or artificial sac) 200.

In applications wherein it is desired to pulverize gallstones within an excised gallbladder, it is desirable to initially aspirate the existing bile or other fluid from the organ and to replace said fluid with clean saline solution. Also, in virtually all applications, it is necessary to make certain that the intracorporeal containment sao is fully liquid filled and contains no air bubbles or voids which could interfere with the efficacy of the size reducing treatment of the material contained within the intracorporeal containment sac. Such infusion and/or aspiration of air, liquid or other material may be effected through side arm 113.

After the liquid has been introduced and/or air aspirated from the sac 200 as desired, latch 107 is depressed so as to disengage the annular groove 121 on cap 119. Cap 119 is then removed from the aspirator/guide cannula 102, leaving the proximal end thereof open.

The elongate cutting instrument of this embodiment is then assembled by attaching the bearing tube assembly 120 to the motor hand piece 117, inserting the proximal end of the drive shaft 140 into the distal end of the bearing tube assembly 120 and advancing the shaft 140 proximally to a point where the lip of seal 148 makes contact with the distal tip of the bearing sleeve 122 (best shown in FIG. 24). A ridge or other stopping means may also be formed near the distal end of shaft 142 so as to abut against or engage the bearing sleeve 122 at a desired stopping point so that the lip of seal 148 is in contact with the end of the bearing sleeve 122 and sufficient compressing force is exerted on seal 148 to prevent leakage thereby. When fully inserted, the proximal end of the drive shaft 140 is operatively inserted into and rotatably engaged by the motor hand piece 117.

After the cap 119 has been removed, the fully assembled elongate cutting tool (i.e. motor hand piece 117, bearing tube assembly 120 and drive shaft/impactor assembly 140 inserted therein) is then grasped by the surgeon and the distal end of the fully assembled elongate cutting tool is inserted into the uncapped, open proximal end of the aspirator/guide cannula 102. The cutting device is advanced downwardly through the cannula body 103 to a point where the proximal hub 130 of the bearing tube assembly 120 is fully nested and seated within the proximal hub 109 of the aspirator/guide cannula assembly 102 and the latch 107 snaps over and engages the shoulder formed on the enlarged portion 131 of the bearing tube assembly 120. As the cutting tool is being advanced to this fully inserted position, the abutment ridges 128a, 128b of the bearing tube assembly 120 will have engaged and pushed the insert body 110 in a distal direction, causing the insert body 110 to advance forward to a point where the distal tip members 106a-106d have become splayed or outwardly pivoted to their desired operative configuration as shown in FIGS. 17 and 18.

Also, when in such position, the impactor 146 will be emergent from the distal opening of the device and will reside in the center of the splayed distal tip members 106a-106d. Accordingly, the splayed distal tip members 106a-106d will serve to form a protective cage assembly around the cutting head or impactor 146 so as to prevent the cutting head or impactor 146 from contacting the surrounding intracorporeal containment sao 200 (e.g. natural organ or artificial sac)

After the elongate cutting tool has been fully inserted through cannula 103, the surgeon will proximally retract the entire device 100 to a point where the open protective assembly 104 will abut against the top of the containment sac 200 or adjacent body wall.

At this point, additional liquid may be added and/or entrained air may be purged once again via port 115 through side arm 113, as there may exist sufficient open space within the cannula to allow passage of liquid or gas between the inner wall of the cannula 103 and the outer Wall of the bearing sleeve 122.

Optionally, the space between the inner surface of the cannula 103 and the outer surface of the bearing sleeve 122 may be sufficiently wide to provide a passageway through which fluid can be infused (distally) and/or fluid and debris may be aspirated (proximally) during or after operation of the cutting tool. Also, the space between the bearing sleeve 122 and cannula 103 may be divided into two or more separate lumens with separate access ports 115 leading into each separate lumen to permit simultaneous or nonsimultaneous infusion and withdrawal through separate lumens while the cutting tool (122 and 140) remains operatively inserted in the cannula 103.

Thereafter, an electric or pneumatic motor within the motor hand piece is energized by depressing trigger 123 to cause the cutting head or impactor 146 to rotate at a desired rate. One motor which is usable in this embodiment is a three-phase DC brushless motor (Altair Instruments, Inc., Ventura, Calif. 93003). The electric or pneumatic motor is sized and adapted to drive the drive shaft at a fixed speed or may be capable of driving the drive shaft at variable speeds as desired. Any rate of rotation may be employed, depending on the particular application. However, as with the first embodiment described above, it is generally preferable that the cutting head or impactor 146 rotate at a rate above 20,000 rpm, typically within the range of 20,000–100,000 rpm. For pulverization of gallstones a rate of approximately 80,000 rpm is preferable. The rotation of the cutting head or impactor 146 will be intermittently or constantly maintained for sufficient time to achieve the desired size reducing treatment of the tissue, stones, or other matter contained within the intracorporeal containment sac 200.

Thereafter, looking catch 107 is manually released and the motor hand piece 117, bearing tube 120 and drive shaft/impactor head 140 assemblies are collectively extracted from the pre-positioned aspirator/guide cannula assembly 102. The cap member 119 is once again placed on the open distal end of the hub portion 109 of the aspirator/guide cannula assembly 102 and the pulverized, liquidized or otherwise treated contents of the intracorporeal containment sao 200 are aspirated via tubular cannula 103, out of infusion/aspiration port 115. Thereafter, the aspirator/guide cannula assembly 102 with the sac 200 affixed thereto is extracted from the body and the existing puncture wound is closed.

v. A Preferred Artificial Containment Sac

In instances where nature has failed to provide a convenient sac-like organ or containment structure for the material which is to be treated, it may be necessary to intracorporeally insert an artificial containment sac into the body and to subsequently place the tissue or other material to be treated within such artificial containment sac. Thereafter, a cutting device such as the device 10, 100 of the present invention may be inserted into the containment sac to effect size reducing treatment and/or removal of the material contained therein.

Figure 28A:
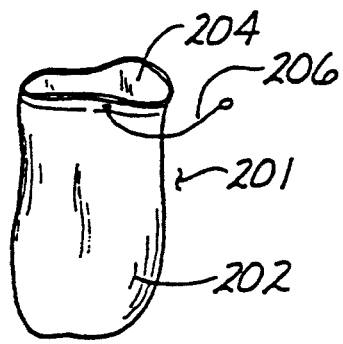
FIG. 28a is a perspective view of a first embodiment of an artificial containment sac of the present invention.

As shown in FIG. 28a, a first embodiment 201 of an artificial containment sac comprises a flexible bag-shaped body 202 having an open top end 204. A closure mechanism, such as a purse string device 206, adhesive strips, zipper, compressible closure mechanism (i.e. a "zip lock" closure) or other type of closure apparatus may be provided to permit closure of the open top end 204 of the bag-like structure 202 after the desired tissue or other material has been positioned therein. In the embodiment shown, the purse string 206 may be pulled by a pair of blunt forceps or other operative instruments inserted into the body cavity. Drawing of the purse string 206 will cause a puckering and closure of the open top end 204 of the bag-like structure 202. Thereafter, the purse string 206 and closed top portion of the bag-like structure 202 may be exteriorized through a small body opening or laparoscopy incision. Thereafter, the purse string 206 may be loosened to permit passage and operation of a device 10, 100 of the present invention within the containment bag 200.

Figure 28B:
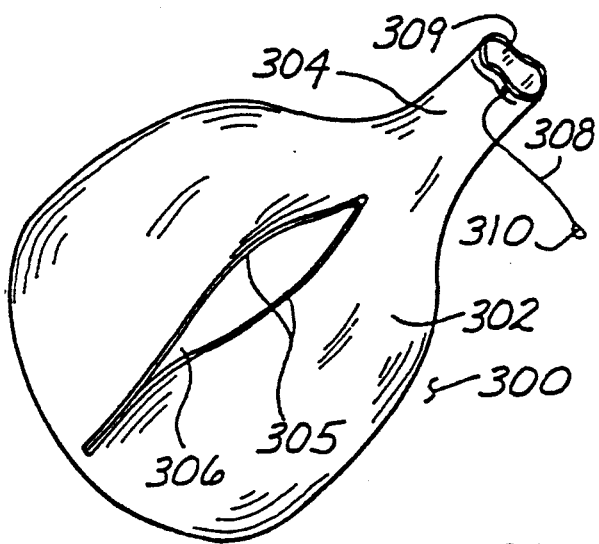
FIG. 28b is a perspective view of a second embodiment of an artificial containment sac of the present invention.

An alternative embodiment shown in FIG. 28b, a larger bag is provided to contain bulkier and larger quantities of material such as large resected tumors, segments of viscera, etc. The embodiment shown in FIG. 28b comprises a bag-like body 302 having an opening 306 formed therein and a relatively narrow neck or tube portion 304 extending therefrom. A closure mechanism such as a zipper, adhesive strips, a compressible (i.e. "zip lock") mechanism 305 or other type of closure apparatus is provided for sealing the opening 306. The narrow neck 304 formed at the top end of the bag-like structure 302 is provided with a purse string, zipper, compressible closure or other type of closure apparatus 308 to permit opening and closing of the neck opening. By such arrangement, the desired tissue or other material may be inserted into the interior of the bag-like structure 302 through the large opening 306 and subsequently the closure mechanism 305 may be compressibly or otherwise closed so as to form a sealed, fluid-tight closure of the bag-like structure. The neck opening at the top end 309 of the neck 304 bag-like structure may also be sealed by the top end closure apparatus 308. The neck portion 304 of the sac 302 may, thereafter, be exteriorized through an existing body, orifice or small incision and the top end closure apparatus 308 may be loosened or opened to permit passage an elongate cutting tool such as that of device 10, 100 through opening 309 and into the interior of the bag-like structure 302.

The purse string closure device 206, 308 of either embodiment of the containment bag may be provided with a ratchet-type locking mechanism such as is found in common plastic tie-wraps, to insure that the opening 204, 309 will remain closed. Complete sealing of openings 204, 306, 309 is particularly important when the tissue contained within the sao 201, 300 is infected, cancerous or contains toxic materials. Thus, the provision of a ratchet-type locking mechanism on a purse string closure 206, 308 will permit the purse string closure 206, 308 to be pulled, thereby effecting closure, but will prevent inadvertent release of the purse string closure device 206, 308 and the consequent opening of the sac 201, 300.

In either of the embodiments shown in FIGS. 28a, 28b or any other conceivable embodiment of the artificial intracorporeal containment sac 201, 300, the sac 201, 300 will be formed of material which is sufficiently pliable and/or constructed to permit folding, compression or collapse of the sac 201, 300 so as to render the sac 201, 300 insertable into a body cavity through an existing orifice or small incision. Additionally, it is desirable that the material of which the sac 201, 300 is formed be sufficiently strong to resist perforation or tearing when the device 10, 100 of the present invention is operatively utilized therewithin.

It is also preferable that the tissue containment sao 201, 300 be formed of material which is biologically compatible and easily sterilizable by radiation, chemical or other means.

Examples of material which may be utilized for formation of an artificial intracorporeal containment bag 201, 300 include latex rubber, chlorofluorcarbons (Gore-Tex ®, Teflon ®), polyethylene, polyurethane, polypropylene and other synthetic materials. Generally such materials will be formed in a pliable film or woven configuration so as to form the desired pliable bag-like structure.

The present invention has been described herein with reference to presently preferred embodiments. It will be appreciated that various additions, deletions, modifications and alterations may be made to the preferred embodiments described herein without departing from the spirit and scope of the invention. For example, any component or element disclosed and described with respect to one embodiment of the invention may, wherever possible, be incorporated into and/or used in connection with the other embodiment. Indeed, many components and elements (e.g. cutting heads/impactors, motor hand pieces, protective assemblies) described herein in connection with one embodiment are usable with the other embodiment and are hereby disclosed as such. Accordingly, it is intended that all foreseeable additions, deletions, modifications and alterations be included within the scope of the following claims.

What is claimed is:

1. A device for morselling material contained within an intracorporeally positioned sac, said device comprising:

a tubular cannula insertable through a body opening into the sac, said cannula having a proximal end, a distal end and at least one lumen extending longitudinally therethrough;

an elongate cutting tool having a rotating cutting head mounted thereon, said cutting tool being insertable through said cannula such that the rotating cutting head is adjacent the distal end of said cannula;

a drive motor connected to said cutting tool for rotationally driving said cutting head to effect morsellation of material which comes into contact with said cutting head;

a rigid protective assembly on the distal end of said cannula, said protective assembly comprising a plurality of rigid tip members movably connected to said cannula and alternately moveable between (i) a "closed" configuration wherein said rigid tip members extend generally forward of the distal end of said cannula and (ii) a "splayed" configuration wherein said tip members diverge apart from one another and outwardly from said closed configuration such that said tip members are spaced apart from one another and form a protective assembly beyond the distal end of said cannula;

said protective assembly being constructed relative to said elongate cutting tool such that, when said elongate cutting tool is inserted through said cannula, said cutting tool will engage and push the protective assembly from its "closed" configuration to its "splayed" configuration, said device including means for limiting the advancement of said rotating cutting head beyond a fully advanced operative position whereat said rotating cutting head is proximal to a distal end of said protective assembly when said protective assembly is in said splayed configuration.

2. The device of claim 1 wherein extraction of the cutting tool from the cannula causes the protective assembly to return to its "closed" configuration.

3. The device of claim 1 wherein said tip members are biased toward said closed configuration and wherein said protective assembly and cutting tool are correspondingly sized and configured such that when inserted through the cannula, said cutting tool will exert pressure on said protective assembly so as to overcome said bias and to cause said protective assembly to move from its "closed" configuration and to its "splayed" configuration.

4. The device of claim 3 wherein said protective assembly and said cutting tool are further sized and configured such that, when extracted from said cannula, said cutting tool will no longer exert pressure on said protective assembly, thereby allowing the biased tip members to return to their "closed" configuration.

5. The device of claim 1 wherein said elongate cutting tool further comprises:
- a generally tubular bearing sleeve having a distal end and a proximal end;
- a rotatable drive shaft extending longitudinally through said bearing sleeve and having said cutting head attached thereto;
- said rotatable cutting head being disposed beyond the distal end of said bearing sleeve.

6. The device of claim 5 wherein said generally tubular bearing sleeve comprises a plurality of ball bearings mounted within a tubular sleeve to facilitate rotation of said drive shaft therein.

7. The device of claim 5 wherein said generally tubular bearing sleeve comprises a plurality of rod-type bearings mounted within said bearing sleeve to facilitate rotation of said drive shaft therein.

8. The device of claim 5 wherein said generally tubular bearing sleeve comprises a plurality of non-rotating bushings mounted within said bearing sleeve to facilitate rotation of said drive shaft therein.

9. The device of claim 1 wherein said tubular cannula further comprises:
- a cap member mountable on the proximal end of said cannula to seal the proximal end of said cannula lumen.

10. The device of claim 1 further comprising a tubular aspiration/infusion port formed in the cannula and in fluid communication with the cannula lumen to permit infusion and aspiration of fluids through said cannula lumen.

11. The device of claim 1 wherein said cannula is sized to pass through a standard laparoscopy portal.

12. The device of claim 11 wherein said cannula is less than 1 cm in diameter.

13. The device of claim 1 wherein said rotatable cutting head comprises first, second, third, and fourth lateral members formed in a cross-configuration.

14. The device of claim 13 wherein said rotatable cutting head further comprises at least one strut extending forwardly from at least one of said lateral members.

15. The device of claim 14 wherein at least two of said lateral members have leading edges which are beveled.

16. The device of claim 14 wherein all lateral members have leading edges which are beveled.

17. The device of claim 14 wherein each strut has a leading edge which is beveled.

18. The device of claim 17 wherein at least one of said lateral members is pitched so as to cause material to be pulled in a proximal direction upon rotation of said cutting head.

19. The device of claim 1 wherein said rotatable cutting head comprises an impactor having a central hub connected to said drive motor and a plurality of impactor elements attached to and extending outwardly from said central hub.

20. The device of claim 1 wherein said protective assembly is formed of plastic material.

21. The device of claim 1 wherein said distal tip members are configured such that when said protective assembly is in said "closed" configuration there remains sufficient open space between said distal tip members to permit aspiration and infusion of fluid and debris therethrough.

22. The device of claim 1 wherein said tubular cannula and said elongate cutting tool are sized relative to one another such that, when said elongate cutting tool is operatively inserted within said cannula, there will remain sufficient space between said cannula and said cutting tool to allow infusion and aspiration of fluid therethrough.

23. The device of claim 1 wherein said tubular cannula is greater than 8 French in diameter.

24. The device of claim 1 wherein said tubular cannula is approximately 1 cm in diameter.

25. The device of claim 1 wherein said cutting head is approximately 0.5–0.9 cm in width at its widest point.

26. The device of claim 1 wherein said drive motor is capable of driving said elongate cutting tool at various speeds.

27. The device of claim 1 wherein said drive motor is a variable speed electric motor.

28. The device of claim 1 wherein said cutting head is a rotational cutting head and wherein said drive motor is attached to said elongate cutting tool so as to rotate said cutting head at least one rotational speed between 20,000 and 100,000 rpm.

29. The device of claim 28 wherein said motor is sized and adapted to drive said cutting head at a speed of approximately 80,000 rpm.

30. A device insertable through an opening in a mammalian body to effect morselling of matter within said mammalian body, said device comprising:
- a tubular cannula insertable through said opening, said cannula having a proximal end, a distal end, a longitudinal axis, and at least one lumen extending longitudinally therethrough;
- a protective assembly formed on the distal end of said cannula, said protective assembly being alternately moveable between a "closed" configuration wherein said protective assembly is sufficiently compact to be inserted through said opening and a "splayed" configuration wherein said protective assembly diverges outwardly from the longitudinal axis of said cannula to define a protective zone within said protective assembly and proximal to a distal end of said protective assembly beyond the distal end of said cannula;
- an elongate morselling apparatus having a distal end whereon a moving head is positioned;
- said morselling apparatus being configured relative to said protective assembly such that the act of inserting said morselling apparatus through said cannula causes said protective assembly to move from said "close" configuration to said "splayed" configuration; and
- said morselling apparatus being insertable, distal end first, into the proximal end of said tubular cannula and advanceable threrethrough, said device including means for limiting the advancement of said moving head beyond a fully advanced operative position whereat said moving head is proximal to the distal end of said protective assembly within said protected zone.

31. The device of claim 30 wherein said protective assembly is spring-biased to said "closed" configuration and wherein said morselling apparatus is configured to exert pressure on said protective assembly in a manner which overcomes said bias and causes said protective assembly to move from its "closed" configuration to its "splayed" configuration.

32. The device of claim 30 wherein said spring-bias of said protective assembly is operative to return said protective assembly from said "splayed" configuration to said "closed" configuration upon extraction of said morsellation apparatus from said cannula.

33. The device of claim 32 wherein said moving head of said morselling apparatus is operative to rotate at a speed between 20,000–100,000 r.p.m.

34. The device of claim 30 wherein said moving head on the distal end of said morselling apparatus comprises a rotating cutting head.

35. The device of claim 30 wherein said opening in said mammalian body is less than 1 cm in diameter, and wherein said protective assembly, is less than 1 cm in transverse dimension when in said closed configuration.

36. The device of claim 30 wherein said protective assembly, is greater than 1 cm in transverse dimension when in said "splayed" configuration.

* * * * *